United States Patent [19]

Poppas

[11] Patent Number: 5,713,891
[45] Date of Patent: Feb. 3, 1998

[54] MODIFIED SOLDER FOR DELIVERY OF BIOACTIVE SUBSTANCES AND METHODS OF USE THEREOF

[75] Inventor: Dix P. Poppas, Brookline, Mass.

[73] Assignees: Children's Medical Center Corporation, Boston, Mass.; V.I. Technologies, Inc., Melville, N.Y.

[21] Appl. No.: 458,885

[22] Filed: Jun. 2, 1995

[51] Int. Cl.$^6$ .................................................. A16B 5/06
[52] U.S. Cl. ............................ 606/2; 606/8; 606/213; 606/214
[58] Field of Search ........................... 606/2, 3, 8, 213, 606/214, 215; 128/897, 898

[56] References Cited

U.S. PATENT DOCUMENTS

| | | |
|---|---|---|
| 4,493,320 | 1/1985 | Treat . |
| 4,672,969 | 6/1987 | Dew et al. . |
| 4,854,320 | 8/1989 | Dew et al. . |
| 5,001,051 | 3/1991 | Miller et al. . |
| 5,156,613 | 10/1992 | Sawyer . |
| 5,209,776 | 5/1993 | Bass et al. ............... 606/214 |
| 5,334,191 | 8/1994 | Poppas . |
| 5,409,148 | 4/1995 | Poppas et al. . |
| 5,409,479 | 4/1995 | Dew et al. . |

FOREIGN PATENT DOCUMENTS

WO91/04073  9/1990  WIPO .

OTHER PUBLICATIONS

"Indocyamine Green Dye–Enhanced Welding with a Diode Laser" by Oz et al; Am. Coll. of Surgeons 1989 Surgical Forum; vol XL pp. 316–318.

Poppas, et al., "Laser Welding in Urethral Surgery; Improved Results with a Protein Solder" *J. Urol.* 139, 415–417 (1988).

Poppas, et al., "Patch Graft Urethroplasty Using Dye Enhanced Laser Tissue Welding with a Human Protein Solder: a Preclinical Canine Model" *J. Urol.* 150, 648–650 (1993).

Poppas, et al., "Preparation of Human Albumin Solder for Laser Tissue Welding" *Lasers in Surgery & Med.* 13, 577–580 (1993).

Choma, et al., "$CO_2$ Laser Urethroplasty in the Rabbit: A Preclinical Model" *Lasers in Surg. & Med.* 12,639–644 (1992).

Poppas, et al., "Chromophore Enhanced Laser Welding of Canine Ureters In Vitro Using a Human Protein Solder; A Preliminary Step for Laparoscopic Tissue Welding" *J. Urol.* 150, 1052–1055 (1993).

Poppas, et al., "Can lasers delivery a sutureless anastomosis to urology?" *Contemporary Urology* 23–32 (Oct. 1993).

Klioze, et al., "Development and Intial Application of a Real Time Thermal Control System for Laser Tissue Welding" *J. Urology* 152, 744–748 (Aug.1994).

Poppas, et al., "Laser Tissue Welding in Genitourinary Reconstructive Surgery: Assessment of Optimal Suture Materials" *Urology* 45(2), 253–257 (Feb. 1995).

Primary Examiner—David M. Shay
Attorney, Agent, or Firm—Arnall Golden & Gregory, LLP

[57] ABSTRACT

Methods for tissue welding using solders incorporating biologically active agents, such as growth factors or hemostatic agents, have been developed. Improved solder compositions have also been defined, yielding greater bursting strength as a function of protein concentration, and through the use of protein unfolding prior to laser-mediated denaturation and coupling. A method for repair of fistulas has been discovered, using water as a chromophore, in combination with solder concentration, to form columns to fill defects where tissue apposition is not possible. Methods have also been adapted for use with other forms of directed energy, including bipolar electrosurgery and light. Examples demonstrate increased strength of repairs by incorporation of growth factors into solders, alone and as a function of solder concentration. Increased adhesion is obtained through prevention of bleeding by incorporation of hemostatic agents such as thrombin or epinephrine, a vasoconstrictor.

17 Claims, 4 Drawing Sheets

MODIFIED SOLDER FOR DELIVERY OF BIOACTIVE SUBSTANCES AND METHODS OF USE THEREOF

BACKGROUND OF THE INVENTION

This is generally in the field of methods for tissue welding using laser mediated coupling of protein solders, and in particular is an improved method and composition incorporating biologically active compounds into the solder.

The use of laser energy to join tissue is referred to as "tissue welding". The goal is to facilitate the joining of tissues with a minimum of scar and good tensile strength of the apposed edges. Lasers that have been used for tissue welding include neodymium:yttrium-aluminum-garnet (Nd:YAG), argon and $CO_2$ lasers. These apparently produce an interdigitation of collagen fibrils, presumably heating at the surface of the tissues which denatures and couples the proteins in the tissue.

Initial studies focused on anastomosis of blood vessels. Later studies looked at other tissues, such as bowel, and nerve repair. The success of tissue union is dependent on several factors, including alignment of the edges of the tissue without tension and in close approximation, adjustment of laser parameters to minimize peripheral tissue destruction and control heating of tissues, and the use of an appropriate protein solder. Various solders such as 40% albumin are described by Poppas, et al., *J. Urol.* 139, 415–417 (1988), Poppas, et al., *J. Urol.* 150, 648–650 (1993), Poppas, et al., *Lasers in Surgery & Med.* 13, 577–580 (1993), Choma, et al., *Lasers in Surg. & Med.* 12, 639–644 (1992), and Poppas, et al., *J. Urol.* 150, 1052–1055 (993). Albumin is a preferred solder since it significantly improves the tensile strength of laser wound closure, as compared to in the absence of solder or the use of blood, it significantly increases the leak point pressure, it is inexpensive and easily manufactured and does not elicit an immunogenic response, and is available in sterile, virus free form. As described in U.S. Pat. Nos. 5,334,191 and 5,409,148 to Poppas, et al., and Poppas, et al. (1993), the solder is further improved through the inclusion of a chromophore such as fluorescein or iron oxide, which increases the absorption of laser energy, reducing the amount of power required to effect a tissue weld, as well as through the use of fine temperature control.

The advantages of tissue welding are numerous, and include rapid (1 mm/second) formation of a fluid tight seal, nonlithogenic, improved healing, reduced wound infection, and shorter hospitalization and improved postoperative results. However, a disadvantage of tissue welding which uses no solder or currently available protein solders, is that the repair has low tensile strength.

It is therefore an object of the present invention to provide methods and compositions for tissue welding which yields repairs having greater tensile strength and improved wound healing properties.

It is another object of the present invention to provide tissue repairs of fistulas and other open areas including ulcers and chronic wounds.

SUMMARY OF THE INVENTION

Methods for tissue welding using solders incorporating biologically active agents, such as growth factors or hemostatic agents, have been developed. Improved solder compositions have also been defined, yielding greater bursting strength as a function of protein concentration, and through the use of protein unfolding prior to laser-mediated denaturation and coupling. A method for repair of fistulas has been discovered, using water as a chromophore, in combination with solder concentration, to form columns to fill defects where tissue apposition is not possible. Methods have also been adapted for use with other forms of directed energy, including bipolar electrosurgery and light.

Examples demonstrate increased strength of repairs by incorporation of growth factors into solders, alone and as a function of solder concentration. Increased adhesion is obtained through prevention of bleeding by incorporation of hemostatic agents such as thrombin or epinephrine, a vasoconstrictor.

DETAILED DESCRIPTION OF THE INVENTION

I. Systems for Energy Mediated Repair

Lasers

Figure 1:
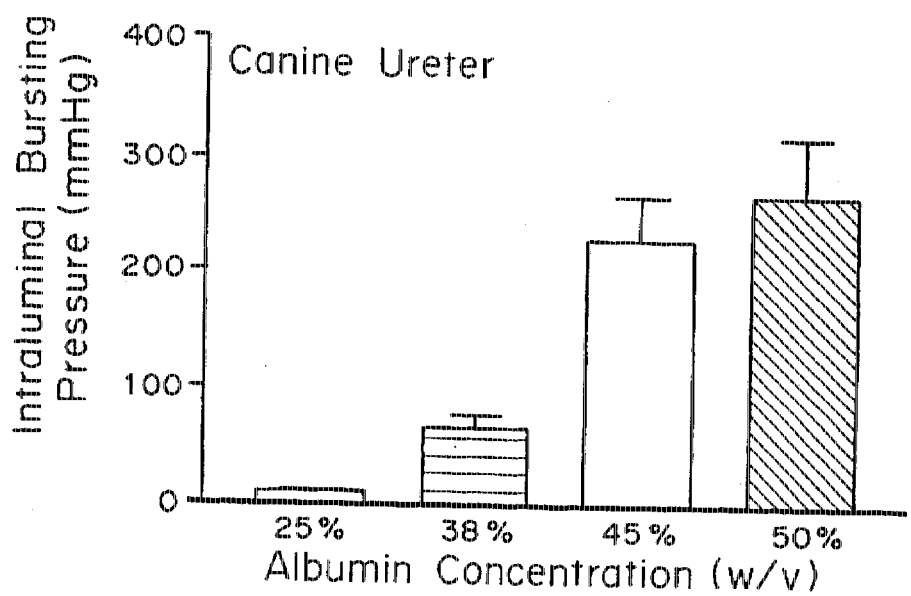
FIG. 1 is a graph showing the effect of albumin concentration on bursting pressure, as a function of intraluminal bursting pressure (mm Hg) for 25%, 38%, 45% and 50% albumin (w/v).

Nd:YAG lasers, GaAlAs lasers, Argon lasers and $CO_2$ lasers can be used for tissue welding. Lasers are commercially available from a variety of companies, such as Laserscope Corp, San Jose, Calif., and are currently in use for a variety of surgical applications. U.S. Pat. No. 5,409,479 to Dew, et al., and U.S. Pat. No. 5,156,613 to Sawyer, incorporated by reference herein, describe the use of lasers and radiofrequency energy to close tissue wounds by tissue welding. U.S. Pat. Nos. 5,334,191 to Poppas, et al., incorporated by reference herein, describes a preferred system for use in tissue welding. As in all surgical procedures, laser welding is most successful when trauma to the surrounding tissue is minimized. Since the laser welding procedure is a non-contact method, the main complications occur when there is extensive thermal injury. The thermal deposition of the laser energy is, therefore, very important to obtain successful laser welds, and the parameters of the laser must be chosen to insure an acceptable thermal profile in the welded tissue.

A suitable laser for use herein is available from ABIOMED R&D Inc., Danvers, MA. ABIOMED R&D Inc. has constructed a laser/infrared thermometer system for welding small vessels at 1.9 µm, a wavelength which achieves maximum penetration into the wall thickness (~0.1 mm) of small vessels and a temperature feedback loop to maintain the weld at a constant temperature to within ±3° C. The console contains a laser diode, with its associated power and drive electronics, and a microprocessor-based data acquisition and control system for monitoring tissue temperature and determining laser power to maintain a constant surface temperature. A removable handpiece, attached to the console via a cable and connector, delivers optical power to the weld site and contains the infrared thermometer. In addition, an audio feedback system is used to inform the surgeon when the desired weld temperature has been reached. Laser power is delivered to the tissue via a 300µm (core diameter) silica fiber. The infrared thermometer used is a direct viewing device, which monitors a 0.3 mm spot in the laser heated region. This spot is imaged directly onto a thermopile using a single ZnSe lens. A small stainless steel tube is used to direct the fiber to the weld site, and a wire guide attached to the end of this tube is used to define the welding region and to provide tactile feedback to the surgeon. The infrared thermometer, consisting of thermopile, imaging lens, and gain and offset electronics is located within the body of the handle.

Other laser welding systems are described in U.S. Pat. Nos. 5,001,051, 4,854,320, and 4,672,969.

Parameters

Absorption and scattering properties of the laser light by the tissue, the composition and physiological state of the tissue, the thermal conductivity of the tissue, the wall thickness, the exposure time, and the laser intensity are all important factors. It has been shown that the acute strength of a weld can be significantly improved if a large fraction of the laser energy is absorbed through the entire depth of the tissue. The maximum acute strength is obtained when the absorption depth of a laser is equal to that of the tissue thickness. Therefore, an optimal weld will result when the penetration depth of the laser light in the tissue is approximately equal to the tissue well thickness. However, chronic outcomes, such as tissue compliance, may well have more desirable characteristics, if the lamina propria is not thermally injured. This can only be achieved with a laser source which partly penetrates the thickness of the tissues. Although this is not desirable for vascular welding, due to the required high initial weld strength, which can be best achieved with a full thickness weld, in other applications such as urologic applications, with a more relaxed initial strength requirement, a partial thickness weld may well be more desirable for long term tissue compliance.

Tissue parameters which can provide diagnostic information for welding include the native auto fluorescence, the optical birefringence, and the temperature of the tissue. A simple Arrhenius model for tissue welding reaction rate (i.e. that the reaction rate increases exponentially with temperature) implies that acceptable welds should be quite sensitive to tissue temperature, providing an excellent real time monitor for the laser welding procedure. By monitoring the tissue temperature during the welding process, the optimal temperature range (that which produces the most desirable clinical outcome) for laser welding can be determined. A feedback loop can be employed to modulate the laser power, maintaining tissue temperature within this optimal range throughout the welding process. This should result in a reproducible, reliable laser weld. Example 1 compares the effects of temperature on acute weld strengths for two laser sources, representative of a tissue thickness matched laser (1.32 µm) and a less penetrating laser (1.9 µm) in bladder tissue. For tissue surface temperatures at, or below, 70° C. no welding occurs; these welds are unable to withstand systemic pressures (catastrophic patency failure). Surface temperatures above 90° C. cause significant tissue shrinkage, causing narrowing and occlusion. Welds are achievable between a temperature range of from 70° C. to 90° C.

Similar results have been obtained using an infrared detector tissue temperature fed back into a PC, which controlled an Argon laser, delivering optical power to the weld site, as demonstrated on rat urethras that were cut and repaired using thermally controlled laser welding ranging in surface temperatures of 50° C. to 90° C. Burst pressures were greatest with a weld temperature of 80° C. However, histological examination of the weld revealed tissue damage at this temperature, which may reduce the life of the weld. Welds at 60° C. and 70° C., though not as strong initially, were still supra-physiological, indicating that these welds may be superior in the longer term. Both studies showed that the tissue surface temperature around 80° C. was preferred for the welding process.

Although the surface temperature is both a convenient and important physical parameter to monitor for tissue welding, it does not provide a complete picture of the welding process. With thick tissue, the surface temperature may reach the desired temperature and be maintained at such a level, while the inner portion of the tissue does not reach an adequate temperature to be welded. In this case, a substantial temperature difference may exist between the outer layer, being monitored, and the inner layers where weld formation is desired. These thermal gradients can be calculated. Since the exposure times are generally long compared to the thermal diffusion times, a steady state solution, with spatially exponential energy deposition and convective heat loss at the tissue surface, should be valid for the welding process. Two wavelengths (1.32 µm and 1.9 µm) represent two extreme penetration depths with respect to the tissue thickness to be welded. For example, in the healthy human bladder, the 1.32 µm laser will penetrate the 2–3 mm tissue, since its penetration depth is around 2.5 mm. Even for a hypertrophic bladder, where the walls may be as thick as 5 mm, or hypotonic condition, a decompensated bladder, with one mm thick walls, the 1.9 µm laser will provide a good comparison, since its tissue penetration depth is low, 0.1 mm, with respect to these thicknesses. Using the 1.9 µm laser diode at weld temperatures of 80° C. or more, is possible with 150 mW to 250 mW of power, when the optical beam is delivered through a 300 µm fiber held 2–3 mm above the tissue. Studies using canine ureters, with approximately 1.5 to 2 mm thick walls, showed a tissue effect at power levels below 500 mW and that welds were achievable with powers of 1 to 1.5 Watts when delivered through a 300 µm fiber placed 3 mm above the tissue. The 1.9 µm laser can be increased in power by one of two methods: a higher power diode (1 Watt is available from SDL and Applied Optronics) or the output of the current diode can be combined with a second, identical diode output into a delivery single fiber.

Bipolar Electrosurgery

Other types of energy can be used instead of lasers. A preferred source is a bipolar electrosurgical device, as described in U.S. Pat. No. 4,493,320 to Treat, the teachings of which are incorporated herein. Radiofrequency energy can also be used, as described in U.S. Pat. No. 5,156,613 to Sawyer, the teachings of which are incorporated herein.

II. Solders

Selection of Materials

The preferred solders are proteins such as albumin, fibrinogen or collagen, which are denatured upon exposure to localized heating up to 80° or 90° C. and crosslinked to each other and the adjacent tissue, to form a weld. Crosslinking can be ionic, covalent, or a mixture thereof.

Concentration

In the preferred embodiment, the protein is applied as a dry powder (in particulate, microsphere, or lyophilized form) or as a solution of between approximately 25% and 50% protein. Typical amounts for repair of a 2 centimeter wound are 50 microliters.

Carriers

Any biocompatible carriers can be used. Aqueous solutions are preferred. Examples include water, saline (0.15 M NaCl), and phosphate buffered saline (PBS). Solders are typically provided in dry or lyophilized form, then reconstituted at the time of use.

Chromophores

Water is a chromophore that can be used to absorb light of a specific wavelength and convert that light to thermal energy.

Other chromophores can be added to the solder. Universal chromophores are black pigments such as india ink and iron oxide. India ink is typically used with lasers such as a Nd:YAG laser emitting a wavelength of 1064 nm. Indocyanine green (ICG) (peak absorption 805 nm) is used with lasers at a wavelength of between 780 and 820 nm, such as the GaAlAs diode laser at a wavelength of 808–810 nm. Fluorescein (peak absorption 496 nm) is used with a YAG laser at a wavelength of 532 nm; methylene blue (peak absorption 661 nm) is used with a laser emitting light at 670 nm. Concentration ranges vary but a typical concentration is approximately 0.54 mM in 50 % albumin. The chromophore is solubilized in the aqueous solution used to reconstitute the lyophilized albumin.

Modifications

The proteins can be modified to increase the amount of crosslinking obtained under particular conditions. In the simplest example, albumin is dialyzed to remove stabilizers used to protect the albumin from denaturation during pasteurization at 60° C. The solder materials can also be chemically modified to decrease folding and increase sites available for crosslinking. For example, albumin can be exposed to a disulfide reducing agent, such as glutathione, 2PDS, or L-cysteine, and the cysteine groups carboxylated, to yield an unfolded protein which is more easily crosslinked.

III. Bioactive Agents

Selection of Materials

A variety of materials can be added to the solder prior to welding, and/or administered after welding. Examples of useful materials include proteins, polysaccharides, nucleic acids, vitamins and metals or ions (calcium, sodium and potassium), and synthetic organic molecules, that retain their biological activity when exposed to up to 80° C heat for between one tenth second and two minutes. Examples include enzymes such as collagenase inhibitors, hemostatic agents such as thrombin, fibrinogen or calcium ions, growth factors, angiogenic factors and other growth effector molecules, bacteriostatic or bacteriocidal factors, antiinflammatories, chemotherapeutic agents or antiangiogenic agents, and vitamins, especially vitamin C.

Growth effector molecules, as used herein, refer to molecules that bind to cell surface receptors and regulate the growth, replication or differentiation of target cells or tissue. Preferred growth effector molecules are growth factors and extracellular matrix molecules. Examples of growth factors include epidermal growth factor (EGF), platelet-derived growth factor (PDGF), transforming growth factors (TGFα, TGFβ), hepatocyte growth factor, heparin binding factor, insulin-like growth factor I or II, fibroblast growth factor (FGF), VEGF, LPA, erythropoietin, nerve growth factor, bone morphogenic proteins, muscle morphogenic proteins, and other factors known to those of skill in the art. Additional growth factors are described in "Peptide Growth Factors and Their Receptors I" M. B. Sporn and A. B. Roberts, eds. (Springer-Verlag, New York, 1990), for example, the teachings of which are incorporated by reference herein.

Growth factors can be isolated from tissue using methods know to those of skill in the art. For example, growth factors can be isolated from tissue, produced by recombinant means in bacteria, yeast or mammalian cells. For example, EGF can be isolated from the submaxillary glands of mice and Genentech produces TGF-β recombinantly. Many growth factors are also available commercially from vendors, such as Sigma Chemical Co. of St. Louis, Mo., Collaborative Research, Genzyme, Boehringer, R&D Systems, and GIBCO, in both natural and recombinant forms.

Examples of extracellular matrix molecules include fibronectin, laminin, collagens, and proteoglycans. Other extracellular matrix molecules are described in Kleinman et al. (1987) or are known to those skilled in the art. Other growth effector molecules include cytokines, such as the interleukins and GM-colony stimulating factor, and hormones, such as insulin. These are also described in the literature and are commercially available.

Collagenase inhibitors, including tissue inhibitor metalloproteinase (TIMP), may also be useful as growth effector molecules.

Examples of hemostatic agents include thrombin, Factor Xa, fibrinogen, and calcium ions, typically in the form of calcium chloride or calcium gluconate. Thrombin is a preferred hemostatic agents since thrombin has many properties useful for wound healing, (i.e. chemotactic to cells such as fibroblasts, mitogenic to various cells) and areas that were missed during the lasing procedure would be plugged due to the coagulant activity of the thrombin. Vasoconstrictive agents such as epinephrine can also be used to contract blood vessels and thereby decrease bleeding. Bleeding at the site of welding is undesirable because it can lead to lower repair strength and visual impairment of the weld field.

Bacteriostatic and bacteriocidal agents include antibiotics and other compounds used for preventing or treating infection in wounds. These are particularly useful when the welding is used at the time of implantation of a prosthetic device.

Concentration

The bioactive agents are typically incorporated in a range of nanograms to micrograms in a volume of 0.1 ml solder solution, although they can also be applied to the wound in dry form, as a paste or suspension. In the examples described below, growth factor is added in a concentration of 500 ng/ml of solder or vehicle. The growth effector molecules are added to the solder in an amount effective to promote wound healing and/or to accelerate or enhance functional strength of the repair.

Method of Administration

The solder is administered at the time of welding, either by brushing, spraying, dripping, or other means known to those skilled in the art. The bioactive agent can be administered simultaneously with the solder, separately or in combination with the solder, or after welding, using the same methods for administration as for the application of the solder.

IV. Conditions and Methods for Treatment

Welding

Welding is used to repair wounds in the tissue where the tissue surfaces can be closely approximated. Tuning the wavelength of the source to match the penetration depth of the tissue being welded, controlling the laser power so that the issue remains at a controlled temperature, the use of albumin as a solder, and proper apposition of tissue are key elements contributing to the successful joining of tissue or vessels without sutures. In a preferred embodiment, the tissues are held in close approximation using sutures, staples or other means known to those skilled in the art. The laser is applied immediately after application of the solder, moving at a rate of approximately 1 mm/second along the wound. Temperature control is maintained to avoid excessive heating which could denature the bioactive agents or cause excessive tissue damage. Selection of the laser and chromophores can be used to effect different laser repairs, for example, by using a laser (1.9 µm) with a short penetration depth (0.1 mm) or a laser (1.32 µm) with a long penetration depth (2.5 mm). Temperature, as demonstrated in the examples, can be used to alter repair strength, as can the inclusion of various bioactive agents. Benefits of laser welding over suturing include shorter operative times, reduced foreign body reaction, reduced bleeding, improved healing, and technical ease of use. For minimally invasive procedures, where conventional suturing is difficult, laser welding of tissue may become a preferred alternative.

Tissue welding can be used with endoscopic surgery. The advantages of endoscopic surgery are obvious. Many procedures can be performed in an office or on an outpatient basis, thereby decreasing the cost and risk to the patient. Recovery rates are increased with these procedures. During a laparoscopic procedure, the surgeon views the area of interest through an endoscope. The two dimensional video image seen by the surgeon makes accurate placement of sutures very difficult, limiting the type of surgeries that can be executed in this manner. Clips and staples are suitable for some laparoscopic procedures, but cannot be used alone in the urinary tract, due to their lithogenic potential and inability to produce a watertight seal. The technique of laser welding of tissue, as an alternative to sutures, alleviates these issues.

A preferred example is the use of tissue welding in laparoscopic bladder augmentation (enterocystoplasty), where a section of bowel is used to increase the volume of the existing bladder. Conventionally, this surgery is performed as an open, transabdominal procedure. The bowel patch is attached to the bladder using standard suture techniques, making the operation difficult to perform laparoscopically. Since the procedure requires a transabdominal incision, the post-operative morbidity and the extent of hospitalization are considerable. Laparoscopic access to the abdomen would avoid the need for a large abdominal incision and potentially reduce the post-operative morbidity in these children. However, tissue approximation by suturing through the laparoscope is difficult and time consuming. The ability to perform watertight closure of tissue using laser welding could significantly improve the capability to approximate tissue laparoscopically. This technology can be adapted to the myriad of urologic procedures currently limited from laparoscopic consideration, due to the extensive need for sutures.

The advantages of laser welding versus sutures are many. Operating times are significantly reduced, especially when dealing with small vessels. Foreign body reaction is minimized, which is especially important in the urinary tract, where the lithogenic potential of clips and staples make them undesirable. The ability of a laser weld to provide a watertight seal, also makes it attractive for use in the urinary tract. It has also been found that, compared to the current microsuturing technique, laser welding shows improved healing.

Repair of Fistulae, Sealing of Lumens

Fistulae are difficult to repair using standard surgical techniques without removal of tissue or the use of general anesthetics, due to epithelialization. In contrast, tissue welding can be used to effect tissue repair without requiring extensive hospital stays using only a local anesthetic. Examples of potential fistulae repair include vesico-vaginal, colo-rectal, and other enteric and cutaneous fistulae. The fistula is filled with solder, preferably in combination with a growth factor, most preferably $TGF\beta_1$. Laser energy is then applied using a wavelength and solder and/or chromophore concentration that causes the solder to polymerize from the bottom up. For example, a 50% albumin solution can be polymerized using a laser with a 1.32 micron light, where the water is the chromophore. A 25% albumin solution under the same conditions would polymerize from the top (i.e., portion closest to the laser) down, which is not as effective. The laser causes the surface of the fistula to "de-epithelialize", allowing the fistula surfaces to heal together.

Other types of lumens that can be sealed include reproductive lumens such as the vas deferens and the Fallopian tubes, using tissue welding instead of surgical ligation. Many other types of repairs can also be effected, including, for examples, repairs of the urogenital systems and gastrointestinal tract.

Sealing of Open Wounds such as Ulcers

Tissue welding can also be used to create "casts" or protective coverings over open or chronic wounds such as decubitas ulcers or other chronic or non-healing wounds. This is achieved by laser welding the solder, preferably in combination with growth effector molecules, over the wound, which may be cleaned to remove necrotic or infected tissue first, either by standard surgical means or using the laser.

The invention will be further understood by reference to the following non-limiting examples.

EXAMPLE 1

Effect of Albumin Concentration and Welding Temperature on Wound Strength

Full-thickness wounds were created with a knife blade in the dorsal skin of pigs. In an attempt to evaluate the effectiveness of wound closure with laser welding, maximal wound stresses were compared in a temperature control study of the optimal welding temperature.

In a first set of experiments, wounds were laser welded using a temperature controlled laser with various concentrations of albumin, 25%, 38%, 45% and 50%. As shown in FIG. 1, wound strength was proportional to albumin concentration, with the greatest strength being obtained with 50% albumin.

In the second set of experiments, wounds were laser welded using a temperature controlled laser with and without 50% human albumin solder (Albuminar-25, Armour Pharmaceutical Co., Kankakee, Ill., lyophilized and reconstituted by adding 8 ml sterile water to 6.45–6.50 g albumin). Welds were performed at 65°, 75°, 85°, and 95° C. With a simple suture cloture as a control, the maximum wound stress for each temperature was evaluated acutely and at 3, 8 and 14 days post-operatively. A 1.32 μNd:YAG laser (Laserscope) was used at less than 2.5 watts, adjusted as necessary to control temperature.

In the acute wounds without albumin solder, there was no significant difference in wound strength at 65°, 75° and 85° C., and only a slight increase in strength at 95° C. In the acute wounds with solder, the maximal wound strength at the lowest temperature (65° C.) was equivalent to the strength at maximal temperature (95° C.) without solder. More importantly in the solder group, the maximal stress increased steadily with increasing temperature to almost double the non-solder strength at 95° C. This indicates that there is a clear advantage in wound strength with the addition of 50% human albumin solder to welds using laser energy alone.

All subsequent chronic animal wounds were closed with albumin solder and compared with a suture control. After 3 days, the temperature versus maximal wound stress relationship was reversed; the wounds gained much more strength at low temperature and were relatively stronger than those at 95° C. (which remained equivalent in absolute strength to the acute wounds). The lower temperature wounds, however, were equivalent in strength to the suture controls. At 8 days, the sutured and low temperature wounds were only slightly stronger than the 95° C. wounds. All wounds gained grossly in strength. By 2 weeks, maximal wound stresses were the same for all temperatures and sutured wounds.

In summary, wounds laser welded with a 50% human albumin solder are significantly stronger than those repaired using laser alone. High temperature closures are acutely stronger than low temperatures. However, high temperature repairs (85° and 95° C.) were found to heal more slowly. By two weeks, all methods of wound closure were equivalent in terms of wound strength.

EXAMPLE 2

Modification of Albumin to Lower Thermal Denaturation Threshold

Figure 2A:
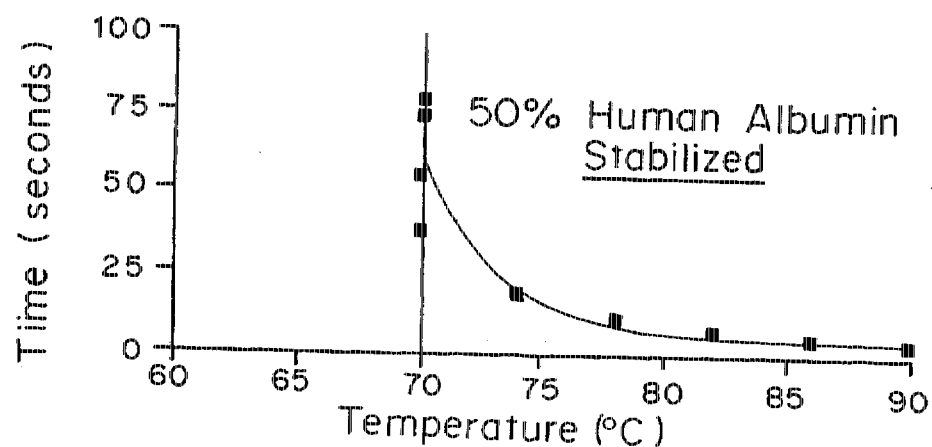
FIG. 2a and 2b are graphs showing how albumin solder can be modified to lower the thermal denaturation threshold, as a function of Time (seconds) versus Temperature (°C.) for stabilized albumin (FIG. 2a) and unstabilized albumin (FIG. 2b).
Figure 2B:
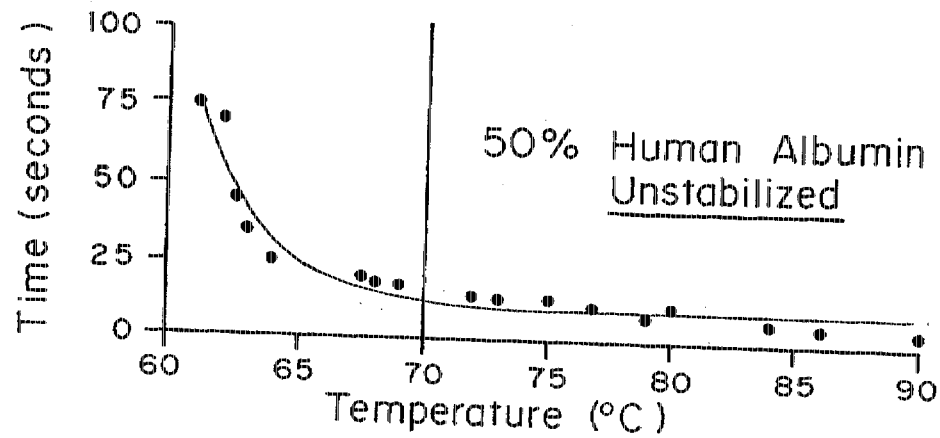

Human albumin is packaged in combination with 0.8 mM Na caprolate and 0.8 mM N-acetyl tryptophane to stabilize the albumin during heat pasteurization. Stabilizers were removed by extensive dialysis into distilled water. Removal of the stabilizers significantly altered the denaturation threshold. A comparison of the albumin prior to treatment with the albumin after treatment is shown in FIGS. 2a and 2b.

EXAMPLE 3

Effect of Incorporation of Growth Factors into Solders

Human recombinant growth factors have been shown to accelerate wound healing in model systems. Studies were therefore conducted to determined whether human albumin can also be used as a time-release delivery vehicle for growth factors for the purpose of accelerating tissue repair after laser-mediated wound closure. A critical requirement for incorporation of these agents was that the growth factors not be denatured by the laser. A thermal controlled laser delivery system (TCL) was used to precisely maintain stable temperatures during welding, thereby avoiding thermal denaturation of bioactive growth factors. Three growth factors, HB-EGF, bFGF, and TGFβ1, were tested in vitro for maintenance of bioactivity after exposure to 80° C. temperature in a water bath or with a TCL using 1.32 μM Nd:YAG laser energy. Maintenance of bioactivity after heating by both methods was demonstrated for each factor using a Balb/C-3T3 mitogenic assay (HB-EGF and bFGF) or a luciferase reporter assay(TGF/$\beta_1$). In vivo experiments were performed to determine the efficacy of growth factor enhanced tissue solder for closure of 2 cm full thickness sutureless dorsal incisions in porcine skin. Incisions were closed using 50 μl of 50% human albumin alone or enhanced with HB-EGF (2 μg), bFGF (10 μg), or TGF-$\beta_1$ (1 μg). Laser welding was performed at 70° C. with a rate of 0.4 mm/second. Suture control wounds were closed with two 5–0 nylon sutures. Five wounds were repaired in each group. Wounds were excised at 3, 5, and 7 days post-operatively. Tensile strength, total collagen content and histology were performed.

Figure 3A:
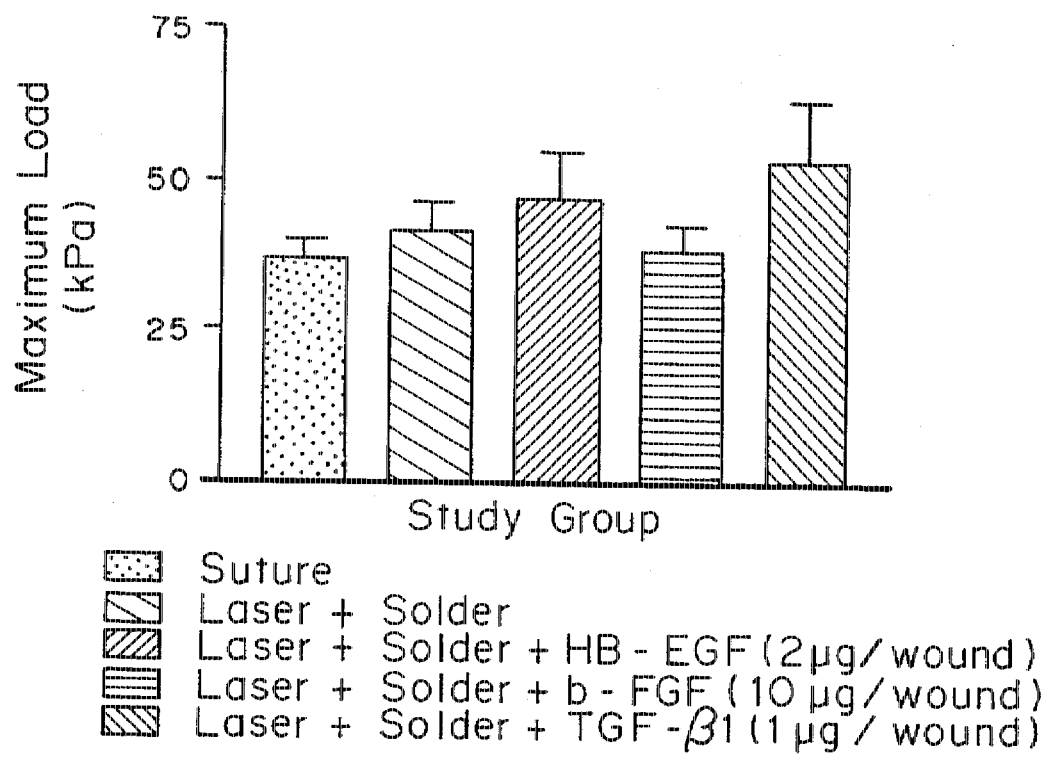
FIGS 3a, 3b, and 3c are graphs comparing wound strength over time, as a function of maximum stress (kPa) for wounds repaired with sutures, laser+solder, laser+HB-EGF, laser+solder+bFGF, and laser solder+TGF$\beta_1$, post-op day 3 (FIG. 3a), post-op day 5 (FIG. 3b), and post-op day 7 (FIG. 3c).
Figure 3B:
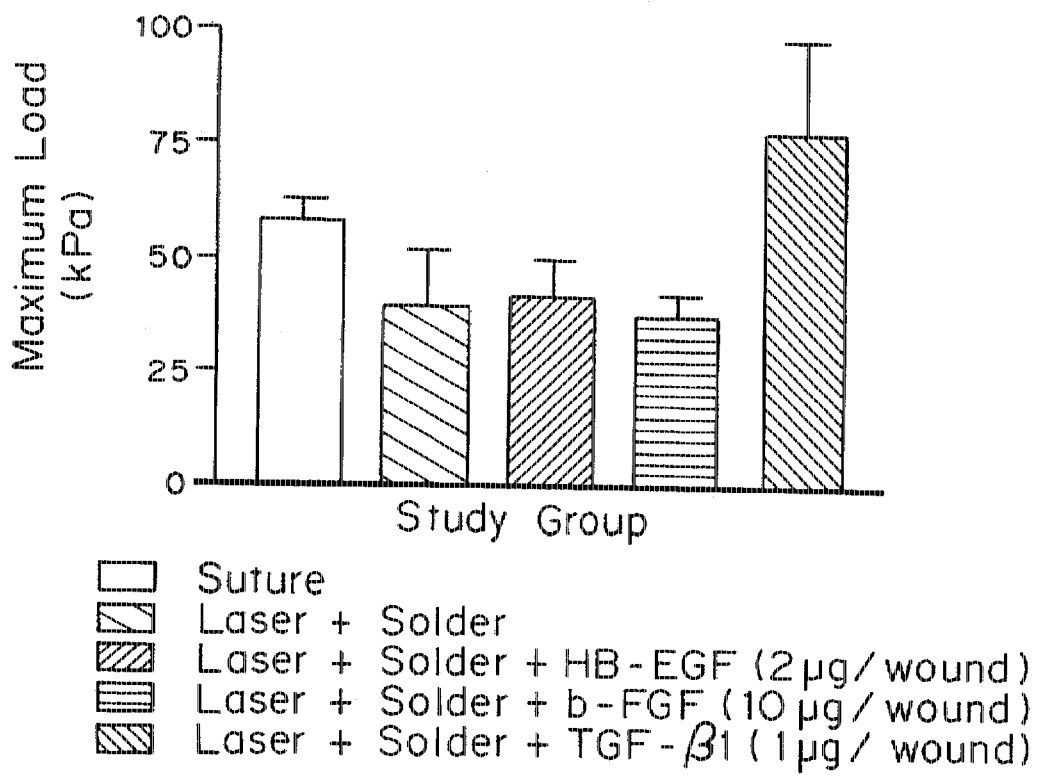
Figure 3C:
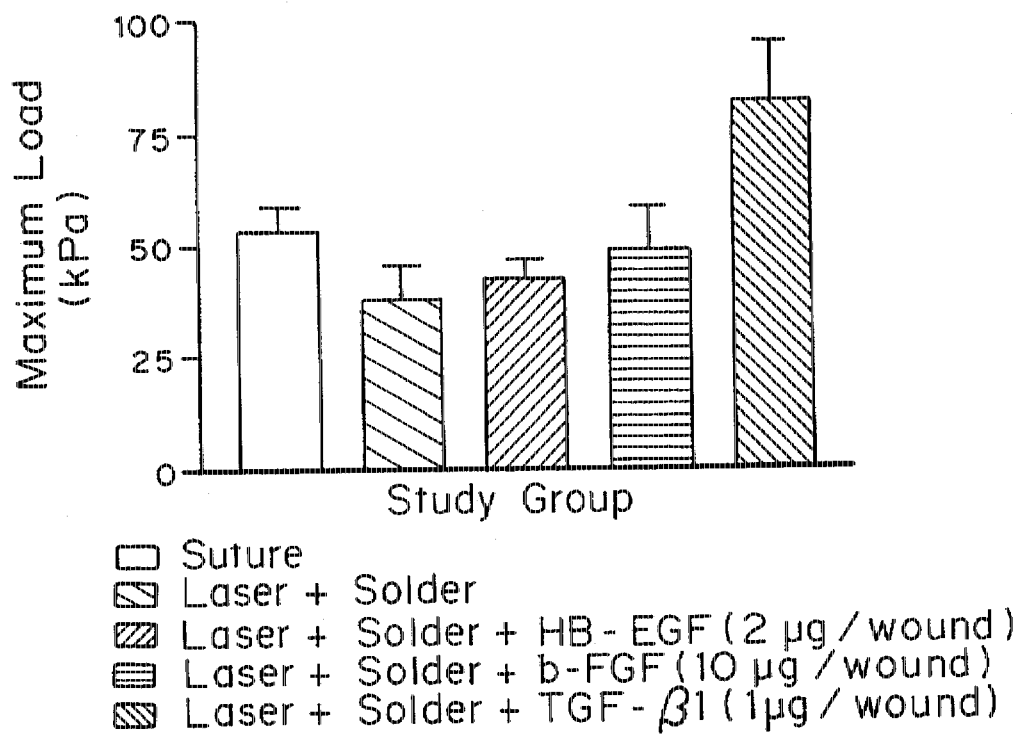
Figure 4:
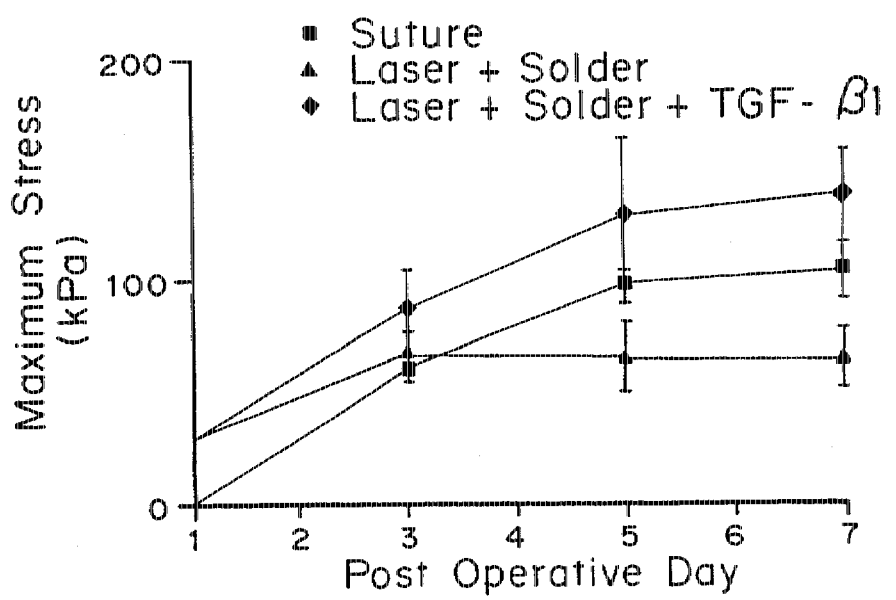
FIG. 4 is a graph comparing repair strength over time, as a function of maximum stress (kPa) versus time, for laser+solder+TGF$\beta_1$ (diamonds), sutures (squares), or laser+solder (triangle).
Figure 5:
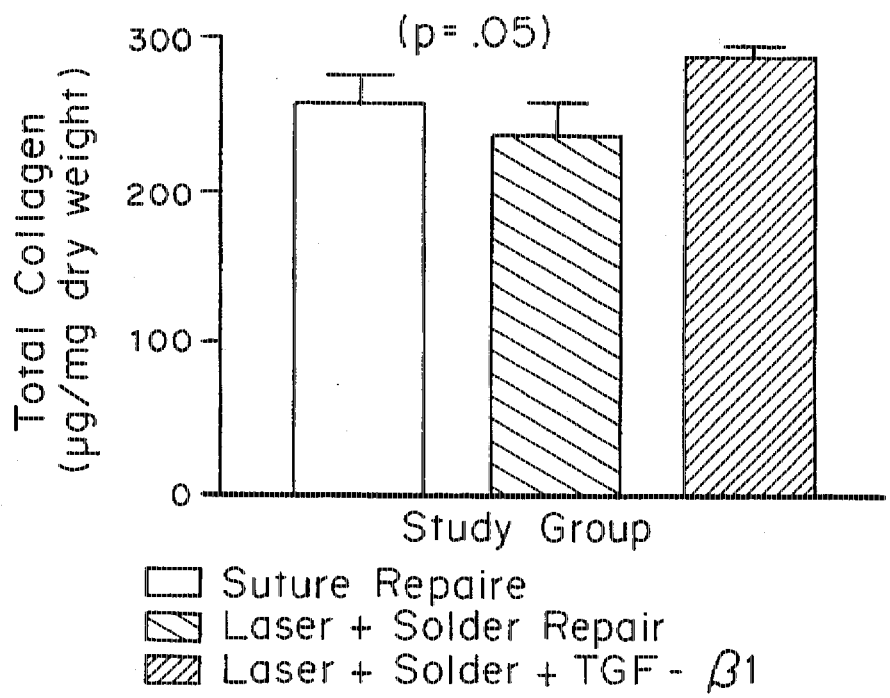
FIG. 5 is graph comparing lasered and non-lasered (sutured) repairs with and without growth factor enhanced albumin solder, as a function of maximum stress (kPa) for sutures alone, sutures+albumin solder, sutures albumin solder+bFGF, sutures+albumin solder+TGF$\beta_1$, laser+sutures+albumin solder, laser+sutures+albumin solder+bFGF, and laser+sutures+solder+TGF$\beta_1$.

The results are shown in FIGS. 3a, 3b, and 3c, comparing repair strength with treatment as a function of time. No significant difference in tensile strength between the groups could be seen at 3 days. By 5 days the tensile strength of the TGF $\beta_1$ group increased by 50% and 25.5% over laser solder alone and suture groups, respectively. At 7 days the TGFβ1 group was 118% and 52% higher than laser solder alone or suture, respectively, as shown by FIG. 4. The HB-EGF and bFGF groups were equivalent to the laser solder group at all time points. As shown by FIG. 5, total collagen content at 7 days increased in the TGFβ1 group by 6% over the suture group and 21% in the laser solder group. Histology confirmed the changes in matrix observed in tensile strength and collagen content. In conclusion, TGFβ1 enhanced albumin solder increases the strength of laser welded wounds and provided a means to accelerate wound dealing, which should decrease postoperative convalescence, hospitalization time, and wound infections.

EXAMPLE 4

Comparison of Growth Factors alone and with Laser Welding

Maximal wound stresses were compared for wounds closed at 70° C. in five groups: suture alone; laser and solder; laser, solder and HB-EGF (2 μg/wound); laser, solder and basic-FGF (10 μg/wound); and laser, solder and TGFβ1 (1 μg/wound). Pigs were sacrificed and wound strength evaluated after 3, 5 and 7 days, as described in Example 3.

Figure 6:
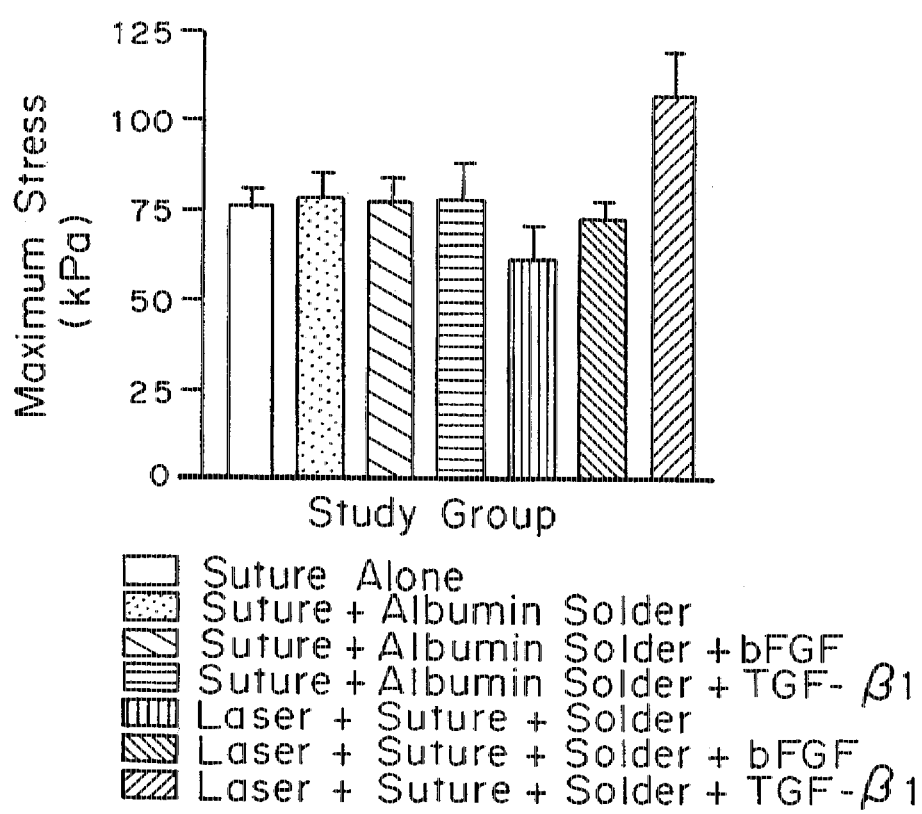
FIG. 6 is a graph of total collagen content (micrograms/mg dry weight) for repairs using sutures alone, laser+albumin solder, and laser+solder+TGF$\beta_1$.

Results are shown in FIG. 6. After 3 days, there was no significant differences in wound strength among groups with the following exception: the TGF treated wounds were slightly stronger than both the suture and bFGF treated wounds. However, at 5 days, TGF treated wounds were significantly stronger than all other wounds and were almost double in strength to the three other groups closed with the laser. By one week, the relationships and absolute wound strengths were similar to those at 5 days. Comparison of the effect of the growth factors in the absence of laser welding demonstrates that the combination of laser welding with TGFβ1 is better than the administration of TGFβ1 alone. The data unequivocally indicate that the addition of TGFβ1 to 50% human albumin solders significantly increases the maximal wound stress at 5 and 7 days compared with other growth factors and sutures alone.

Modifications and variations of the present invention will be obvious to those skilled in the art from the foregoing detailed description. Such modifications and variations are intended to come within the scope of the appended claims.

I claim:

1. An improved protein solder wherein the protein is unfolded by treatment with reducing agents followed by blocking of free cysteines by reaction with carboxylating or methylating reagents.

2. An improved solder wherein the protein is heat stabilized albumin, and the heat stabilizing compounds are removed from the albumin prior to exposure to light or radiofrequency energy.

3. An improved method for joining tissue using energy to weld a solder formed of a protein denatured upon exposure to localized heating at less than 90° C., the improvement comprising mixing with and administering to the site where the protein solder is applied, a therapeutically effective amount of a therapeutic bioactive agent having biological activity after exposure to 80° C. heat for at least one tenth second, selected from the group consisting of proteins, polysaccharides, nucleic acids, vitamins, and synthetic organic molecules, and welding the protein solder by exposure to a temperature up to 80° C. heat.

4. The method of claim 3 wherein the bioactive agent is administered in an amount effective to promote wound healing, accelerate or enhance functional strength of the repair, inhibit infection or decrease bleeding at the site.

5. The method of claim 3 wherein the bioactive agents are selected from the group consisting of enzymes, hemostatic agents, growth effector molecules, bacteriostatic or bacteriocidal factors, antiinflammatories, chemotherapeutic agents, anti-angiogenic agents, and vitamins.

6. The method of claim 5 wherein the growth effector molecules are selected from the group consisting of growth factors and extracellular matrix molecules.

7. The method of claim 6 wherein the growth factors are selected from the group consisting of epidermal growth factor (EGF), platelet-derived growth factor (PDGF), transforming growth factors (TGFα, TGFβ), hepatocyte growth factor, heparin binding factor, insulin-like growth factor I or II, fibroblast growth factor (FGF), VEGF, LPA, erythropoietin, nerve growth factor, bone morphogenic proteins, muscle morphogenic proteins, and cytokines.

8. An improved solder formed of a protein denatured upon exposure to localized heating at less than 90° C. for use in tissue welding, the improvement comprising a therapeutically effective mount of a therapeutic bioactive agent having biological activity after exposure to 80° C. heat for at least one tenth second, selected from the group consisting of proteins, polysaccharides, nucleic acids, vitamins, and synthetic organic molecules, to promote wound healing, accelerate or enhance functional strength of the repair, inhibit infection or decrease bleeding at the site.

9. The solder of claim 8 wherein the bioactive agent is present in an amount effective to promote wound healing, accelerate or enhance functional strength of the repair, inhibit infection or decrease bleeding at the site.

10. The solder of claim 8 wherein the bioactive agents are selected from the group consisting of enzymes, hemostatic agents, growth effector molecules, bacteriostatic or bacteriocidal factors, antiinflammatories, chemotherapeutic agents, anti-angiogenic agents, and vitamins.

11. The solder of claim 10 wherein the growth effector molecules are selected from the group consisting of growth factors and extracellular matrix molecules.

12. The solder of claim 11 wherein the growth factors are selected from the group consisting of epidermal growth factor (EGF), platelet-derived growth factor (PDGF), transforming growth factors (TGFα, TGFβ), hepatocyte growth factor, heparin binding factor, insulin-like growth factor I or II, fibroblast growth factor (FGF), VEGF, LPA, erythropoietin, nerve growth factor, bone morphogenic proteins, muscle morphogenic proteins, and cytokines.

13. The solder of claim 8 further comprising a chromophore capable of converting light energy from the laser to thermal energy.

14. A method for repairing open or chronic wounds comprising applying to the wound a solder formed of a protein denatured upon exposure to localized heating at less than 90° C., applying to the wound an effective amount of growth effector molecules to promote wound healing or to accelerate or enhance functional strength of the repair, and applying electromagnetic energy to the solder to denature the protein under conditions wherein the activity of the growth effector molecules is retained.

15. The method of claim 14 wherein the growth effector molecules are applied in the protein solder.

16. A method for repairing a fistulae or filling a lumen comprising administering into the fistulae or lumen a solder formed of a protein denatured upon exposure to localized heating at less than 90° C., wherein the concentration of the solder allows passage of energy prior to denaturation, and exposing the solder to electromagnetic energy at a wavelength under conditions wherein the energy passes through the solder to cause denaturation at the point furthest from the energy source moving towards the energy source as a function of denaturation or solidification of the solder.

17. The method of claim 16 wherein the protein solder is 50% albumin in aqueous solution.

* * * * *